United States Patent
Ohana et al.

(10) Patent No.: US 7,233,002 B2
(45) Date of Patent: Jun. 19, 2007

(54) SPECT GAMMA CAMERA WITH A FIXED DETECTOR RADIUS OF ORBIT

(75) Inventors: Israel Ohana, Haifa (IL); Shoulamit Cohen Shwartz, Atlit (IL)

(73) Assignee: Ultraspect Ltd., Haifa (IL)

( * ) Notice: Subject to any disclaimer, the term of this patent is extended or adjusted under 35 U.S.C. 154(b) by 106 days.

(21) Appl. No.: 10/904,756

(22) Filed: Nov. 25, 2004

(65) Prior Publication Data
US 2006/0108532 A1 May 25, 2006

(51) Int. Cl.
*G01T 1/166* (2006.01)
(52) U.S. Cl. ............................................... 250/363.04
(58) Field of Classification Search ............ 250/363.04
See application file for complete search history.

(56) References Cited

U.S. PATENT DOCUMENTS

| 5,444,252 | A | 8/1995 | Hug et al. | |
|---|---|---|---|---|
| 5,486,700 | A | 1/1996 | Silberklang et al. | |
| 5,554,848 | A | 9/1996 | Hermony et al. | |
| 5,717,212 | A | 2/1998 | Fulton et al. | |
| 5,739,539 | A * | 4/1998 | Wang et al. | 250/363.04 |
| 5,777,332 | A | 7/1998 | Lonn et al. | |
| 5,929,446 | A | 7/1999 | Plummer et al. | |
| 6,943,355 | B2 * | 9/2005 | Shwartz et al. | 250/363.04 |
| 2003/0208117 | A1 | 11/2003 | Shwartz et al. | |
| 2006/0124855 | A1 * | 6/2006 | Gagnon | 250/370.09 |

OTHER PUBLICATIONS

Bouwens et al. "Resolution recovery for list-mode reconstruction in SPECT." Physics in Medicine and Biology, vol. 46, No. 8 (Aug. 2001), pp. 2239-2253.*

Zeng et al. "Iterative reconstruction of fluorine-18 SPECT using geometric point response correction." Journal of Nuclear Medicine, vol. 39, No. 1 (Jan. 1998), pp. 124-130.*

Anderson et al. "Improving wrist SPECT with fanbeam collimators and an MLEM algorithm." IEEE Nuclear Science Symposium Conference Record, vol. 4 (Oct. 16-22, 2004), pp. 2548-2552.*

J. A. Patton, T. F. Budinger, "Single Photon Emission Computed Tomography". From the book "Diagnostic Nuclear Medicine, Fourth Edition", edited by M. P. Sandler, J. A. Patton, F. J. TH. Wackesr A. Gottschalk. Lippincott Williams & Wilkins, Philadelphia 2003.

(Continued)

*Primary Examiner*—David Porta
*Assistant Examiner*—Frederick F. Rosenberger
(74) *Attorney, Agent, or Firm*—Shalom Wertsberger; Saltamar Innovations

(57) ABSTRACT

The current invention presents designs of SPECT gamma cameras without the in-out mechanical motion of the detectors. The elimination of this motion is achieved by the implementation of iterative algorithms, such as Resolution Recovery and/or Wide Beam Reconstruction, which compensate for the Line Spread Function effect due to the collimator characteristics. The use of these methods enables construction of SPECT gamma cameras with a range of novel designs, having their gamma detector (or detectors) orbiting the patient in a predetermined orbit of fixed radius. For example, the radius might be chosen as such that the majority of all patients can be scanned by the system. The advantages of the invention are applicable for gamma cameras with any numbers of detectors.

36 Claims, 11 Drawing Sheets

OTHER PUBLICATIONS

Doumit DAOU, Isabelle Pointurier, Carlos Coagila, Didier Vilain, Abdel Wahab Benada, Rachida Lebthai, Thierry Fournme, Michel Slama, and Dominique Le Gluludec, "Performance of OSEM and Depth-Dependent Resolution Recovery Algorithm for the Evaluation of Global Left Ventricular Function in 201 TI Gated Mycrocardial Perfusion SPECT", published in the Journal of the Nuclear Medicine, vol. 44, No. 2, Feb. 2003.

* cited by examiner

Fig. 4. (Art)

Fig. 5. (Art)
a.                    b.

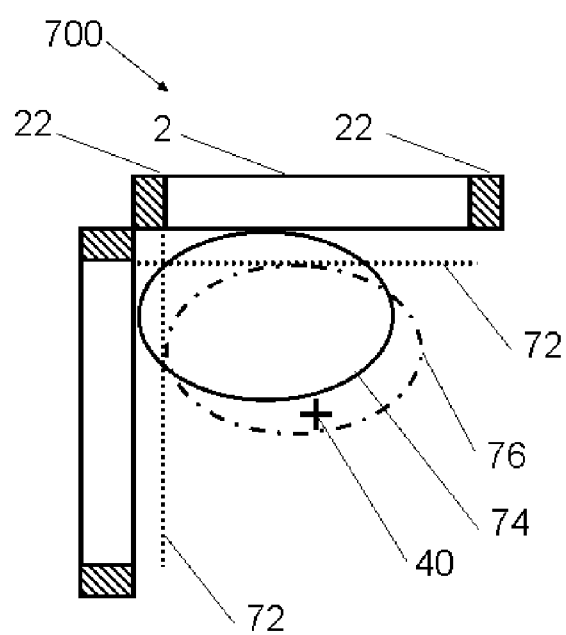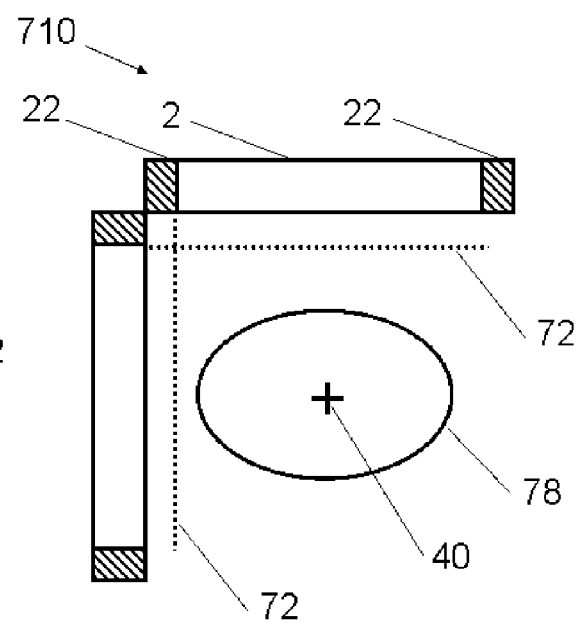
Fig. 7. a. (Art)  Fig. 7. b.

SPECT GAMMA CAMERA WITH A FIXED DETECTOR RADIUS OF ORBIT

FIELD OF THE INVENTION

The present invention is related generally to the design of nuclear gamma camera wherein the detector motion follows a fixed, patient-independent orbit.

BACKGROUND OF THE INVENTION

Single photon emission (SPE) imaging is a known medical imaging technique. It involves injecting radiopharmaceutical substance into a patient's body and evaluating the distribution of the radiopharmaceutical substance, which is indicated by the distribution of gamma rays emitted from within the patient's body.

A radiation-detecting system, often referred to as Gamma camera, detects those gamma rays. Gamma camera detects gamma rays emitted from the radiopharmaceuticals substances, and the data acquired is analyzed to form an image representing the distribution of concentrations of the radiopharmaceutical substance within a specific body area.

Several modalities of SPE imaging are in use. One of them is Single Photon Emission Computerized Tomography (SPECT). In this technique the gamma camera rotates around the region of interest of the patient's body, and data are collected at several angular positions (angular projections). A fully three dimensional image is formed. SPECT is considered to be a very useful technique and a good tool for obtaining diagnostic information, however it requires the collection of large number of emitted photon (large statistics) and this means that in order to obtain the required number of photons, a long acquisition time is necessary. Long acquisition time means that the patient is subjected to a relatively long period of discomfort and furthermore, making the overall number of patients who can be imaged in a given time relatively small—a feature that many medical institutes and hospitals regard as extremely unfavorable and undesirable.

Gamma camera generally comprises a photon detector crystal coupled with a plurality of photomultiplier tubes, or an array of solid-state detectors combined with position logic circuits and data analysis apparatus. A collimator for limiting the angle of incident gamma rays is incorporated with the gamma camera. Collimators are used to limit the detection of photons to a predetermined range of incidence angles (photons with greater incidence angles are absorbed by the collimator septa). A collimator typically includes thousands of square, round or hexagonal parallel channels, through which, and only through which, gamma rays are allowed to travel and reach the detector. Generally, a parallel-hole collimator is in use, however various other arrangements may be used.

As gamma rays are emitted from the radiopharmaceutical substance, they travel through the collimator, unabsorbed and interact with the detector, which is placed directly adjacent to the collimator. The interactions of the gamma rays with the detector crystal create flashes of light in a process called scintillation. The scintillation light is preferably detected by an array of photomultiplier tubes, which are normally coupled to the back of the crystal. Photomultiplier tubes are used when a very small amount of light is emitted in scintillation. The output signals from the photomultiplier tubes are electric pulses, proportional to the energy of the gamma rays. The electric pulse output is received by position logic circuits, which determine the position where the scintillation event had occurred on the detector. Similarly, in solid-state detectors including solid-state crystals, the incident photons produce electric current corresponding to the energy of the incident photon in the specific location of incidence. This current is picked up by electrodes coupled to the solid-state crystals and is processed. The data is processed by position logic circuits and is transferred to a processing computer in order to process the data into readable image of the spatial distribution of the radiopharmaceutical substances within the patient's body.

The main limitations to the quality of SPECT images come from limited number of registered gamma ray photons and the geometric resolution of the collimator. Intrinsic resolution of the detector plays a small role.

One of the most important components of current SPECT and Planar gamma camera is the collimator, which in practice defines system resolution and system sensitivity. The narrower the angular acceptance-range of the collimator, the better the resolution, but also the fewer the number of collected photons. Resolution is thus limited by sensitivity, and vice versa. High-resolution collimators typically used in the art reject photons arriving to the detector at angles larger than about 2 degrees (relative to the direction perpendicular to the detector from surface), while high-sensitivity collimators reject those at angles larger than about 3 degrees. The camera spatial resolution depends on the geometric resolution of the collimator, and degrades with distance between the surface of the collimator and the organ being imaged. The system's resolution, which depends on the distance is called Line (or point) Spread Function (LSF) of the collimator.

The system's sensitivity has a very weak dependency on the distance between the collimator and the emitting object.

In cameras used in the art, in order to get the best resolution for a given application (and with a given collimator) the distance between the collimator and the human body, which emits the photons, was kept as small as possible. Therefore, the position of the detector relative to the patient table is adjusted for each patient according to its physical dimensions.

Thus, very costly mechanical and electronic features are incorporated into a typical SPECT/Planar camera used in the art in order to enable the detector/collimator ensemble to get as close as possible to the patient's body. The detectors on these cameras are supported by a mechanical articulation device having multiple axis of motion. In most SPECT cameras, this usually includes the possibility to rotate the detector and to move it towards the patient (In) and away from the patient (Out). In few SPECT cameras with two detectors, where the in-out motion is disabled or restricted, the patient is brought to close proximity to the detector using elaborate table motion which includes up-down as well as left-right motion.

Some of the clinical procedures are done with a fixed radius of rotation, namely: the radius of the detectors does not change during the SPECT scan. The radius of rotation in this mode is determined for each patient and it mostly depends on the physical dimensions of the patient. In other modes of operation that exist in modern design, the radius of rotation for all or each of the detectors is changed as a function of the angular position.

These features are sometimes termed "body contouring". During the scan, the detectors, while orbiting the patient's body get close to the body and follow the contour of the body while acquiring the data. In some of the SPECT gamma camera the "body contour" is designed as a pre-study (or learn mode) feature, namely; the radius for each rotating angle is studied before the scan followed by the real study with a radius dependent orbit. In other SPECT gamma cameras this is an on-line automatic feature that senses the patient contour and determines the closest possible radius for each angle.

The mechanical motion unit of the detector enables an "In and out" motion of the detector and collimator, i.e., it enables the detectors to get close to the body and to retract in areas where the patient body circumference is larger.

In a dual head camera, this in-out motion may be independent for each detector or the motion can be synchronized between the two heads and the patient bed.

Some dual head cameras are built wherein their two detectors are arranged so that their surfaces are substantially at right angle to each other during the scan. This configuration, known as "L mode" is the preferred configuration for cardiac examination. In this configuration, the independent motion of the detector is inhibited by the necessity to avoid collision between the detectors. Often the two detectors are fixed to each other and are moved as one unit. Performing body countering in L mode cameras is more complex and usually requires side-to-side motion of the bed.

In many modern systems one may find an automatic electronic element that keeps and controls the distance between the detector and the patient's body to a minimum while scanning the patient contour in either SPECT or Planar application.

The mechanical parts are costly and have many safety features built into them in order to avoid collision with the patient body while getting close to the body, i.e., while performing the in-out motion in orbit. Furthermore, these features increase the complexity of the electromechanical system and the complexity of the software that controls the motion, thus reducing the reliability of the camera.

The need for in-out motion of the detector and collimator ensemble does not permit many system design configurations that may have been more efficient than the classical single/dual/triple head configurations.

Some gamma camera systems of four detector-heads are known in the art. These systems are with a relatively very small Field of View (FOV) and are dedicated for brain applications. The typical sizes of the detectors are 25×25 $cm^2$.

The process of recovering the three dimensional image from the acquired data is called SPECT reconstruction. Various types of SPECT reconstruction algorithms exist in the art. Generally these algorithms belong to one of two types:

1) Non-Iterative Reconstruction Methods:

Non-iterative (direct) reconstruction algorithms such as Filtered Back Projection (FBP) algorithms typically approximate the path of the gamma rays impinging the detector, by assuming parallel rays, thereby ignoring the LSF effect in the reconstruction and provide images in which the resolution is dominated by the collimator LSF effect.

2) Iterative Reconstruction Methods:

Iterative reconstruction algorithms search for solution that matches the acquired data. One of these algorithms is known as the Maximum Likelihood Expectation—Maximization (MLEM) method which attempts of find the solution that most matches the acquired data, based on the likelihood principle. Another method, which has an underlying similar mathematics is the Ordered Subset Expectation Maximization reconstruction (OSEM). This method was developed in order to reduce the computation time of the MLEM, which is computation intensive. Other iterative reconstruction algorithms include the block iterative reconstruction methods.

There are two main approaches to iterative reconstruction: Noise suppression and Resolution Recovery/Wide Beam Reconstruction. The most commonly used iterative reconstruction algorithms, such as OSEM yields noise suppression. These methods typically assume parallel rays, thereby ignore the LSF effect.

The Resolution recovery (RR) and/or Wide Beam Reconstruction (WBR) iterative methods (RR/WBR for short) allow for a priory knowledge of different physical dimensions of elements that exist in the data acquisition system to be integrated into the solution-measurements matching process. Accounting for the LSF effect together with the consideration of physical dimensions of the elements that control the effect, allow for the implementation of a mathematical solution to reduce or eliminate this effect.

The RR/WBR algorithms for compensation for the LSF effect in SPECT and/or Planar gamma camera are known in the art.

US Patent published patent application US-2003-0208117 (published on 6 Nov. 2003), titled "SPECT GAMMA CAMERA" which is incorporated herein by reference, discloses the WBR iterative reconstruction method and includes references for other iterative methods known in the art.

Currently both approaches to iterative reconstruction are focused on enhancing image quality by improving image resolution and reducing the noise. None of these approaches challenged the gamma camera mechanical design.

U.S. Pat. No. 5,554,848 (Hermony, et al. Sep. 10, 1996) titled "Gantry for nuclear medicine imaging systems" demonstrated the complexity of the gantry of nuclear cameras used in the art.

U.S. Pat. No. 5,486,700 (Silberklang, et al. Jan. 23, 1996) titled "Proximity controls for gamma camera" discloses a proximity controls for controlling the proximity of a gamma camera to a patient during a scan of the patient.

U.S. Pat. No. 5,777,332 (Lonn, et al. Jul. 7, 1998) titled "Automatic patient alignment during nuclear imaging body contour tomography scans" discloses a methods and systems for performing a tomographic scan which allow an operator to define a non-circular orbit so that a detector can be positioned close to a patient at each view.

U.S. Pat. No. 5,444,252 (Hug, et al. Aug. 22, 1995) titled "Adjustable dual-detector image data acquisition system" discloses an improved image acquisition system which allows the angular displacement between two detectors and a patient table capable to be displaced vertically and horizontally from a lateral axis to allow the body of a patient to be positioned next to the detectors and to improve resolution.

U.S. Pat. No. 5,717,212 (Fulton, et al. Feb. 10, 1998) titled "Three detector head gamma camera system with independently circumferentially positionable detector heads", discloses a gamma camera comprising a rotating gantry, three gamma detector heads which are mounted to the rotating gantry and a linear motors selectively moves each detector head along the tracks to change its circumferential position relative to the other detector heads.

U.S. Pat. No. 5,929,446 (Plummer, et al. Jul. 27, 1999) titled "Configurable multiple detector nuclear medicine gantry" discloses a transformable gamma camera including several detectors, each of the detectors is radially movable with respect to the rotating gantry's axis of rotation.

SUMMARY OF THE INVENTION

According to the present invention, a SPECT gamma camera employs WBR or RR SPECT image reconstruction algorithms thus eliminating the need for in-out mechanical motion of the detectors. The use of this method enables construction SPECT gamma cameras with a range of novel designs, having their gamma detector (or detectors) orbiting the patient in a predetermined orbit of fixed radius. For example, the radius might be chosen as such that the majority of all patients can be scanned by the system.

In the currently known single, dual and triple SPECT gamma camera design, the use of the method according to the invention, enables elimination the mechanical and electronic components that involved with the in-out motion, hence reducing system cost and complexity and dramatically improving its safety level. Additionally, elimination of mechanical elements may reduce system weight, system size or system footprint, making the system more adaptable to small clinics and doctor's offices.

Additionally, in currently used gamma cameras, preparation for imaging includes setting up the radius of rotation and optimal positioning of the bed. In the embodiments of the current invention, this part of the set-up time may be saved.

Specifically, in the field of cardiology there is a growing need for small, low cost gamma camera.

In a triple-head SPECT gamma camera, the present invention enables (in addition to the above) increasing the detector size. For example to 50 cm, eliminating the effect of patient partial coverage, which happens if the size of the detector is smaller than the width of the patient. In such a case, during SPECT scan radiation from at least part of the patient body does not reach the detector. The missing information yields incompleteness of the SPECT data and result in image artifacts.

In some embodiment of the present invention, the gamma camera includes according to a preferred embodiment a four head SPECT gamma camera with detectors size greater than 25×25 cm. For example, essentially the same detectors that are in use in dual head camera, with axial dimension of 40 cm and transaxial dimension of 54 cm may be used. In this embodiment of the invention, a gamma camera with four large detectors covers all SPECT applications with no degradation in image quality while reducing the acquisition time due to the added detectors.

A system with three, four or more large detectors, would enjoy very high sensitivity compared with systems used today. High sensitivity would allow reduction of acquisition time. Short acquisition time can be translated to high patient throughput or to enable following the dynamics of radiopharmaceuticals within the patient.

According to one aspect of the present invention, there is provided method for SPECT imaging comprising: acquiring data related to gamma photons from a patient who received a dose of radiopharmaceutical substance, using at least one gamma detector orbiting in a predetermined fixed radius with respect to the patient; analyzing the data and reconstructing SPECT image using an iterative algorithm.

Optionally, the patient is stationary during data acquisition.

Optionally, reconstructing SPECT image using an iterative algorithm takes into account the attenuation of the patient.

According to another aspect of the invention, there is provided a SPECT gamma camera system, comprising: at least one gamma detector adapted to orbit in a predetermined fixed radius with respect to a patient; analyzer connected to said at least one gamma detector, for analyzing data collected from said at least one gamma detector and reconstructing a SPECT image, using an iterative algorithm.

Optionally, a stationary bed is provided for the patient to lie on during data acquisition.

Optionally, plurality of detectors is provided.

Optionally, the system further includes means for obtaining transmission image of the imaged subject, and the iterative reconstruction algorithm take into account information obtained from transmission image in order to correct the emission image.

In a preferred embodiment, a fan beam collimator associated with one detector is constructed so that its focus line 64 is substantially near the adjacent edges of the other two detectors. In this embodiment, the FOV of the detector marked by the dashed lines 62 (for clarity shown here for only one of the three detectors), substantially fills the volume between the detectors.

These and other objects and advantages in accordance with the present invention will become more readily apparent from a consideration of the ensuing description, claims, and accompanying drawings.

BRIEF DESCRIPTION OF THE DRAWINGS

An exemplary embodiment of the invention is described in the following section with respect to the drawings. The same reference numbers are used to designate the same or related features on different drawings. The drawings are generally not drawn to scale.

FIGS. 7.*a* and 7.*b* show a nuclear gamma camera equipped with two detectors in L mode configuration; FIG. 7.*a* demonstrates the missing data caused by close proximity. The orbit is complex for a non-circular object.

DETAILED DESCRIPTION OF EXEMPLARY EMBODIMENT

The following detailed description is of the best presently contemplated modes of carrying out the present invention. This description is not to be taken in a limiting sense, but is made merely for the purpose of illustrating the general principles in accordance with the present invention. The scope of the present invention is best defined by the appended claims.

Figure 1:
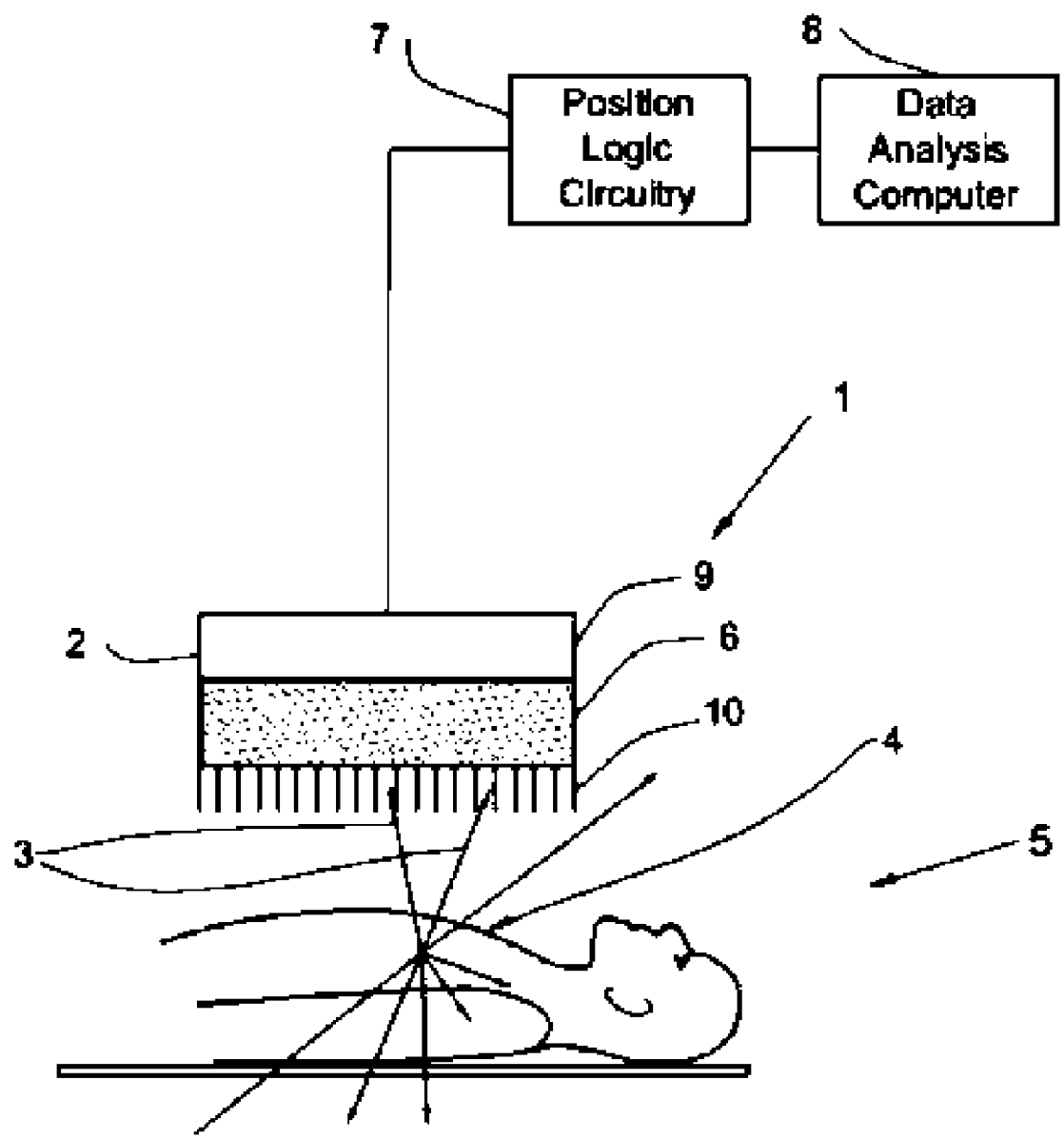
FIG. 1 is a pictorial illustration of the operation of a gamma camera in accordance with the present invention.

Reference first is made to FIG. 1, depicting a side view of a simplified schematic diagram of gamma camera in accordance with the present invention, for obtaining a SPECT image of a portion of a body that has been administered by a radiopharmaceutical substance which radiates gamma rays.

The gamma camera 1 comprises at least one detector 2 mounted above an inspected portion 4 of a body 5, a position logic circuitry 7 and a data analysis computer 8, all connected appropriately.

Detector 2 includes at least one photon detector crystal 6 facing the portion 4 of body 5. The photon detector crystal 6 may be in the form of a semiconductor crystal or crystals. This crystal(s) may be selected from a first group including Cadmium-Telluride (CdTe), Cadmium-Zinc-Telluride (CZT), Lead Iodine (PbI).

The detector 2 of the gamma camera 1 may further include at least one photo-multiplier 9. The photon detector crystal(s) in this case may be selected from a second group including Sodium Iodine (NaI), Bismuth Germanate (BGO), Yttrium Oxyorthosilicate (YSO), Cerium-doped Lutetium Oxyorthosilicate (LSO) and Cesium-Iodine (CsI) with solid-state photo-diode or avalanche photo-diode (APD).

Detector 2 is capable of rotating around trajectory relative to the body to acquire data at multiple predetermined positions from multiple views around the body. Alternatively, the detector may rotate continuously during the scan.

Detector 2 is provided with means 10 establishing angles of incidence of gamma rays on the detector in a restricted range. It is noted that by angle of incidence it is meant the angle between the perpendicular to the surface of the detector and the ray path.

Such means may be in the form of appropriate collimators. However, these means should be such as to allow the gamma rays having various incident angles in the range of 0 to 5 or more degrees. The collimator holes may be symmetric, such as circular or hexagonal shaped holes, or have different dimensions along the different axis, such as ellipse or rectangular shape holes. Furthermore, the shape of the bore of the collimators may be cylindrical, conic or other converging shapes.

In operation, detector 2 acquires radioisotope gamma ray photons 3, which are emitted from portion 4 of body 5 and passing through means 10. The gamma photons impinge the photon detector crystal 6. If the crystal 6 is a semiconductor crystal selected from the first group specified above, then the crystal converts the photons into electric signals, which are fed into a position logic circuitry 7 for processing. Alternatively, if the crystal is selected from the second group specified above, i.e. is of the kind that utilizing photo-multipliers, then the crystal converts photons 3 into scintillation light, which is, thereafter, transformed into electric signals by photo-multiplier 9.

As a result of the processing, the electric signals are transformed into data indicative of photon energy and positions on the photon detector crystal 6 in which the photons impinge the detector. The data that includes the position at which each photon impinged the detector, for each position of the detector, is termed projection. Thereafter, the projections are fed into a data analysis computer 8 for the purpose of reconstructing an image of a spatial distribution of the pharmaceutical substance within the portion of the body by processing said data. The photon energy information is registered for the assessment of the amount of Compton scattering that is introduced in the acquisition. In general, there is one energy window around each peak of the radiopharmaceutical substance. The width of each window is preferably set as narrow as may be reasonable to the specific detector that is used, in order to reject as many scattered photons as possible.

The reconstruction of the image according to the present invention may be performed based on any appropriate existing algorithm, however, it should necessarily be based on an iterative algorithm taking into account the major elements that affect the LSF of the system and correcting for it. For example, the reconstruction of the image might be a WBR or RR algorithm.

Figure 2:
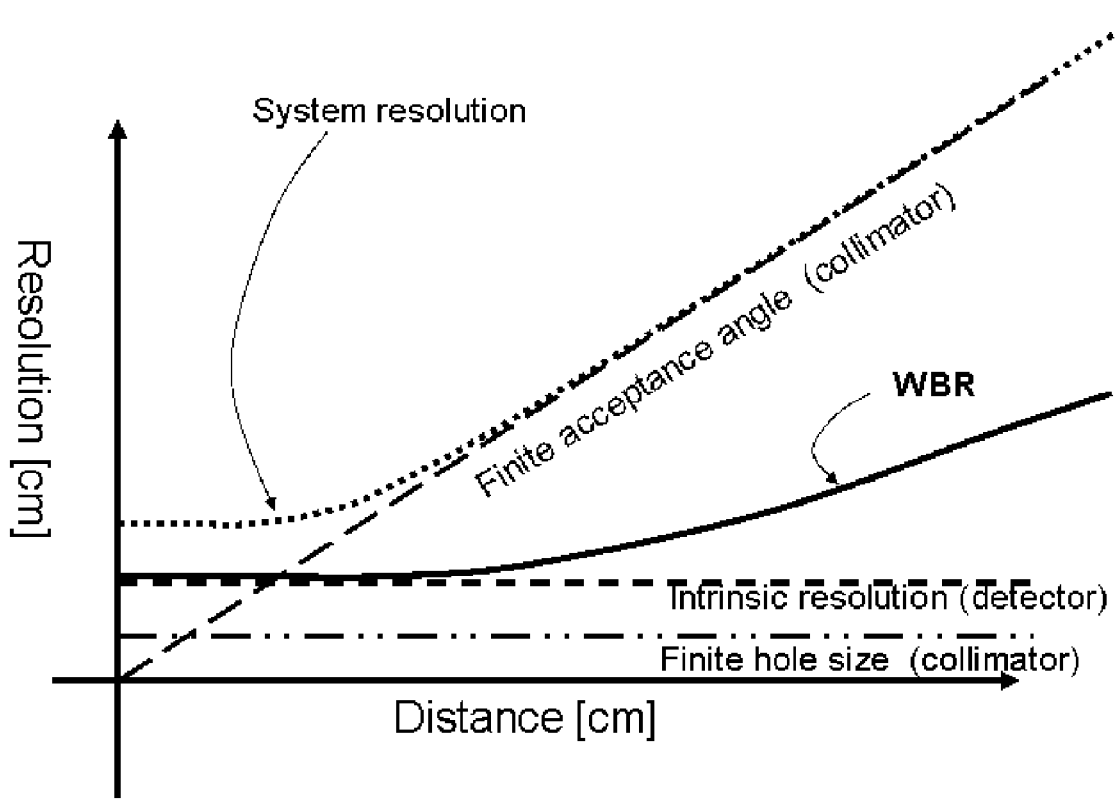
FIG. 2 is a graph showing schematic representation of resolution degradation of a gamma camera image with distance between the detector and the imaged object.

Reference is made to FIG. 2, showing a graph of schematic representation of resolution degradation of a gamma camera image with distance between the detector and the imaged object. When using non-iterative reconstruction methods, resolution limiting effects such as: finite collimator hole size, detector intrinsic resolution and finite acceptance angle of the collimator, adds up substantially in quadrate. Beyond a certain distance, the collimator acceptance angle dominates the resolution, and the system resolution degrades essentially linearly with the distance between the surface of the detector and the imaged object.

Figure 3:
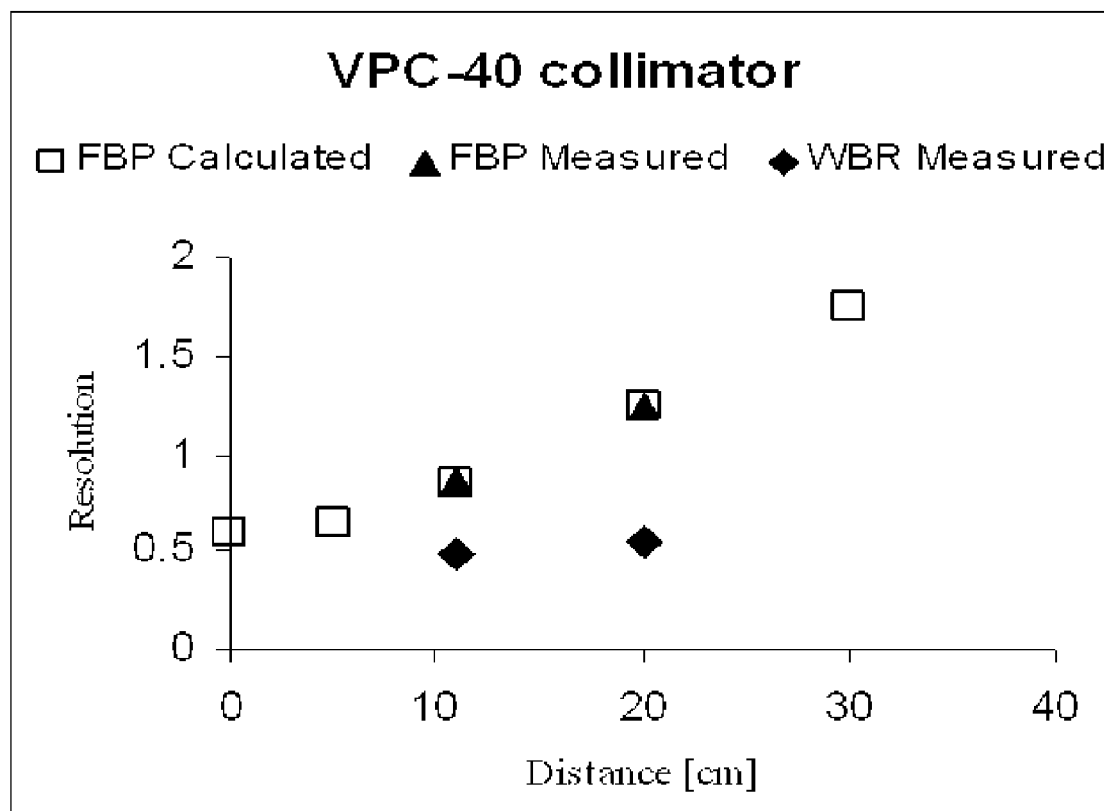
FIG. 3 shows actual values calculated and measured for a specific gamma camera equipped with a specific collimator in accordance to FIG. 2.

FIG. 3 shows actual values calculated and measured for a specific gamma camera equipped with a specific collimator in accordance to FIG. 1.

System resolution in cm is plotted against the distance between the test object and the surface of the collimator. A Tc99m isotope was used with VariCam camera (Elscint Ltd.) equipped with a VPC-40 collimator for the test. A VPC-40 collimator is made of parallel hexagonal bores each defined by Lead septa of 0.2 mm thickness and 31 mm height and 1.5 mm between adjacent bore centers.

Open squares are resolution values for FBP reconstruction algorithm calculated using physical model of the system according to FIG. 1.

Closed triangles are resolution values actually measured for the system from data reconstructed using FBP algorithm. As can be clearly seen, the calculated resolution values match the values measured using FBP algorithm.

In closed diamonds are resolution values actually measured for the same system from data reconstructed using WBR algorithm. As can be clearly seen, the WBR resolution values are much smaller than the FBP resolution values. The graph also indicates that the slope of the WBR resolution values is smaller. Thus, small, clinically useful resolution is attainable at larger distances. Similar experimental results were obtained for other collimator types.

Figure 4:
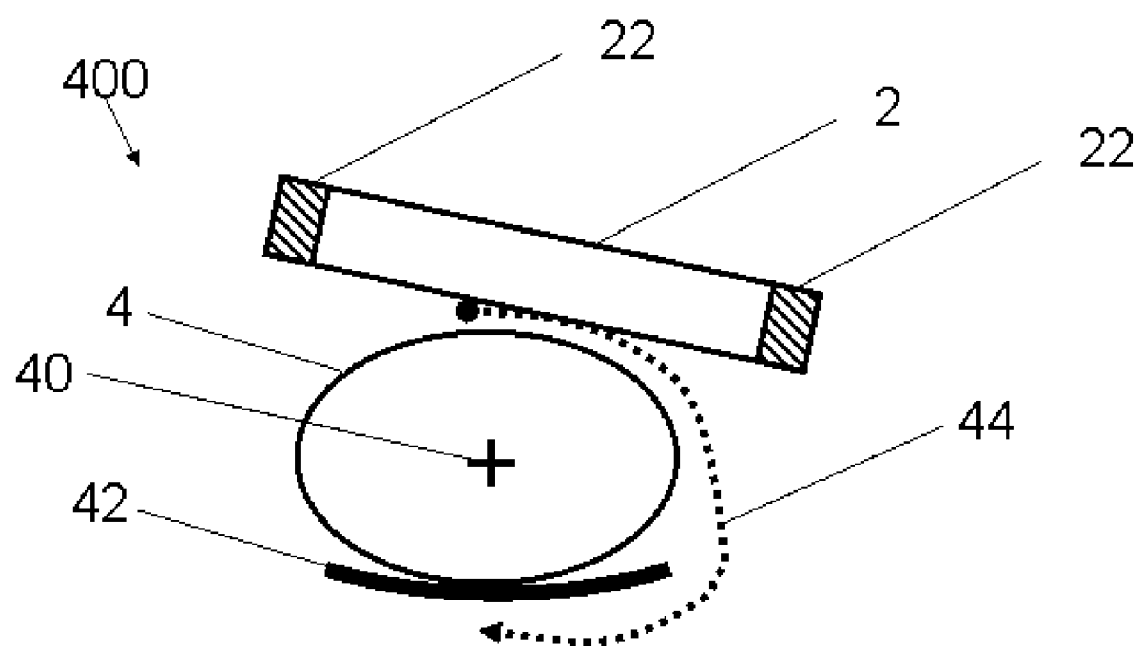
FIG. 4 is a schematic representation of the non-circular orbit of a gamma camera detector as used in the art.

Reference is now made to FIG. 4, depicting an axial view of a simplified schematic diagram of gamma camera used in the art, for obtaining a SPECT image of a portion of a body that has been administered by a radiopharmaceutical substance which radiates gamma rays. In this example, system 400 comprises a single detector 2 rotating around inspected portion of the body 4, which is placed on patient table 42. The geometric center 40 of the camera is marked with a cross. In practice, the operator often uses the up-down motion of patient table 42 to approximately align the center of the inspected portion 4 with the geometric center 40.

Detector 2 is equipped with a collimator (not shown). Detector 2 has insensitive zone around its perimeter where gamma radiation cannot be recorded. For detectors based on NaI scintillation crystal and PMT array, this dead zone is few cm wide and is approximately half the diameter of the PMT used. For solid-state detectors, the dead zone is smaller and is due to the casing of the detector, which is made of gamma absorbing material thick enough to shield the detector from radiation not passing through the collimator.

In order for detector 2 to stay as close as possible to the inspected portion 4 while orbiting around it, it moves following a non-circular orbit 44 (partial orbit of only 180 degrees are shown in this example, but other angular ranges are used in the art). As can be seen, non-circular orbit 44 is complex due to the fact that inspected portion 4 is not round and the existence of patient table 42.

An elaborate mechanical system has to be used to enable the detector to follow the complex non-circular orbit. Both rotation and radial motions are necessary to accomplish this orbit.

Figure 5:
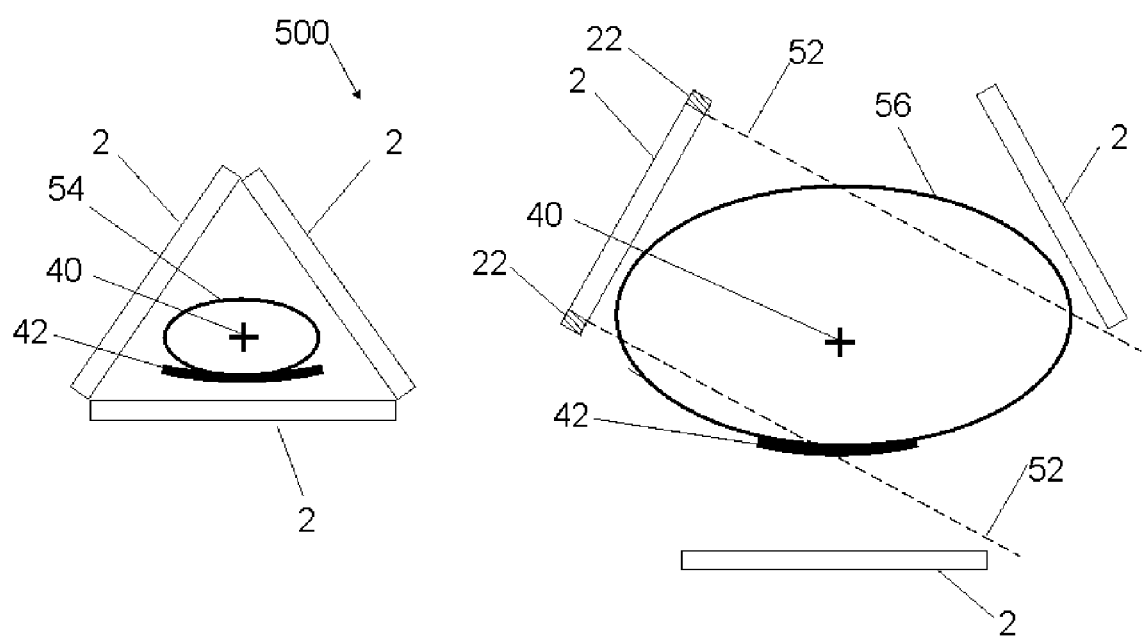
FIGS. 5.*a* and 5.*b* show a nuclear gamma camera equipped with three detectors, demonstrating the limitation on detector size and the resulting missing data for large objects as used in the art.

Reference is now made to FIGS. 5.*a* and 5.*b*, depicting an axial view of a simplified schematic diagram of a gamma camera used in the art, shown here in two configurations. In FIG. 5.*a*, system 500 comprises three detectors 2 rotating around inspected portion of a small body 54, which is placed on patient table 42. In FIG. 5.*b*, the system is configured to rotate around inspected portion of a large body 56. The geometric center 40 of the camera is marked with a cross. In practice, the operator often uses the up-down motion of patient table 42 to approximately align the center of the inspected portion of the body with the geometric center 40.

Detector 2 is equipped with a collimator (not shown). Detector 2 has insensitive zone 22 around its perimeter where gamma radiation cannot be recorded.

As can be seen in FIG. 5.*a*, the size of detectors 2 poses a limitation on how close detectors 2 may get to the geometric center 40 and thus an unavoidable gap remains when imaging a portion of a small body 54 such as a baby or a person's head. Small size detectors have to be used to allow close proximity to small objects. Currently available triple head systems use smaller detectors than preferably used in dual head systems.

In contrast, FIG. 5.*b* depicts the same system 500 when configured to image a portion of a large body 56. In this configuration, some parts of the inspected object may be situated outside the Field Of View (FOV) of the detector marked by the dashed lines 52 (for clarity shown here for only one of the three detectors).

As a consequence, three-headed gamma camera may need to be optimized for objects of limited range of sizes.

Figure 6:
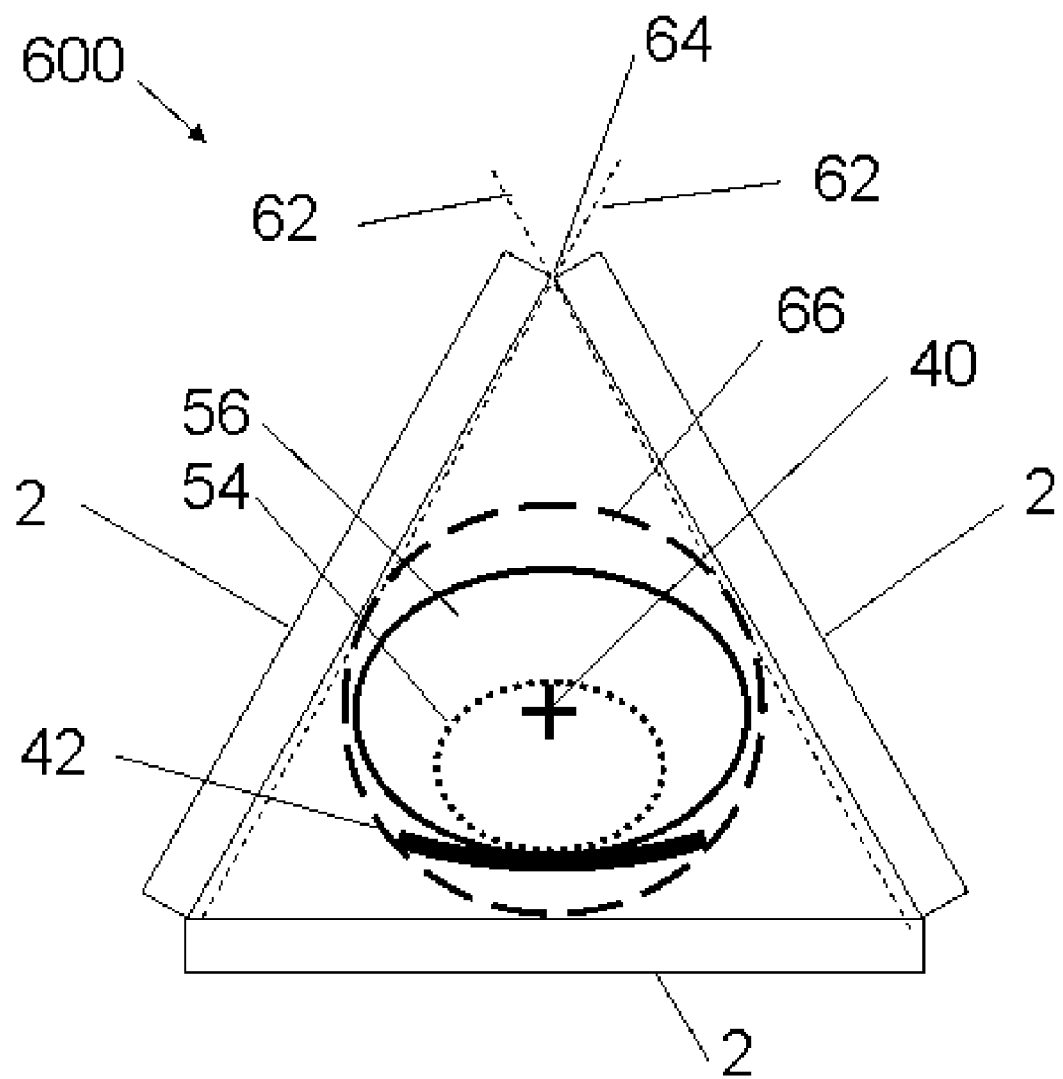
FIG. 6. depicts an embodiment of the current invention showing a nuclear gamma camera equipped with three detectors.

Reference is now made to FIG. 6, depicting an axial view of a simplified schematic diagram of gamma camera according to an embodiment of the current invention. In this embodiment, system 600 comprises three detectors 2 in a fixed configuration, rotating around inspected portion of a body, which is placed on patient table 42. The same configuration is used for inspected portion of a small body 54 or inspected portion of a large body 56. The geometric center 40 of the camera is marked with a cross. In this embodiment, patient table 42 may be fixed in one position for all sizes of inspected portion of the body; preferably in low position so large objects could be inspected.

Alternatively patient table may be equipped with up-down motion system.

Detector 2 is equipped with a collimator (not shown). Detector 2 may have insensitive zone (not shown) around its perimeter where gamma radiation cannot be recorded.

As can be seen in FIG. 6, the size of the detectors 2 is not limited by the necessity to be close to the inspected body, thus large size detectors, for example 40 to 50 cm or more in the transaxial dimension may be used for small as well as large objects.

Optionally, one, two or all the detectors may be fitted with different types of collimator. In this embodiment, the reconstruction algorithm uses the different parameters indicative of the physical properties of each collimator type.

Optionally, at least one of the detectors is fitted with a fan-beam or cone-beam collimator. The usage of these collimators increases the number of photon counts, which improves sensitivity.

In a preferred embodiment, a fan beam collimator associated with one detector is constructed so that its focus line 64 is substantially near the adjacent edges of the other two detectors. In this embodiment, the FOV of the detector marked by the dashed lines 62 (for clarity shown here for only one of the three detectors), substantially fills the volume between the detectors.

Optionally, a cover 66 prevents physical contact between the moving detectors 2 and the patient, eliminating possibility of patient injury and the need for safety measures.

Reference is now made to FIG. 7.*a* and FIG. 7.*b*, depicting an axial view of a simplified schematic diagram of a dual head gamma camera as used in the art and according to an embodiment of the current invention respectively.

In FIG. 7.*a*, system 700 comprises two detectors 2 each may include insensitive zones 22 around its perimeter where gamma radiation cannot be recorded. In the system used in the art, best image resolution is achieved when the inspected portion of the body is in close proximity 74 to the surface of the detector 2. However, part of the inspected portion in close proximity 74 lie outside the borders of the missing data 72. Thus, it is customary to move the inspected portion to an unobstructed proximity 76, thus sacrificing some resolution. The unobstructed proximity is adjusted before the scan and often non-circular orbit maintain it during scan.

FIG. 7.*b*. depicts an axial view of a simplified schematic diagram of a dual head gamma camera according to an embodiment of the current invention.

System 710 according to the embodiment of the current invention comprises of the same elements, but in contrast to art system 700, in inventive system 710, the centered inspected portion 78 is substantially centered on the systems' center of rotation 40.

System 710 does not require mechanical elements needed to move the centered inspected portion 78 from its position or elements needed to change the orbit of detectors 2.

Figure 8:
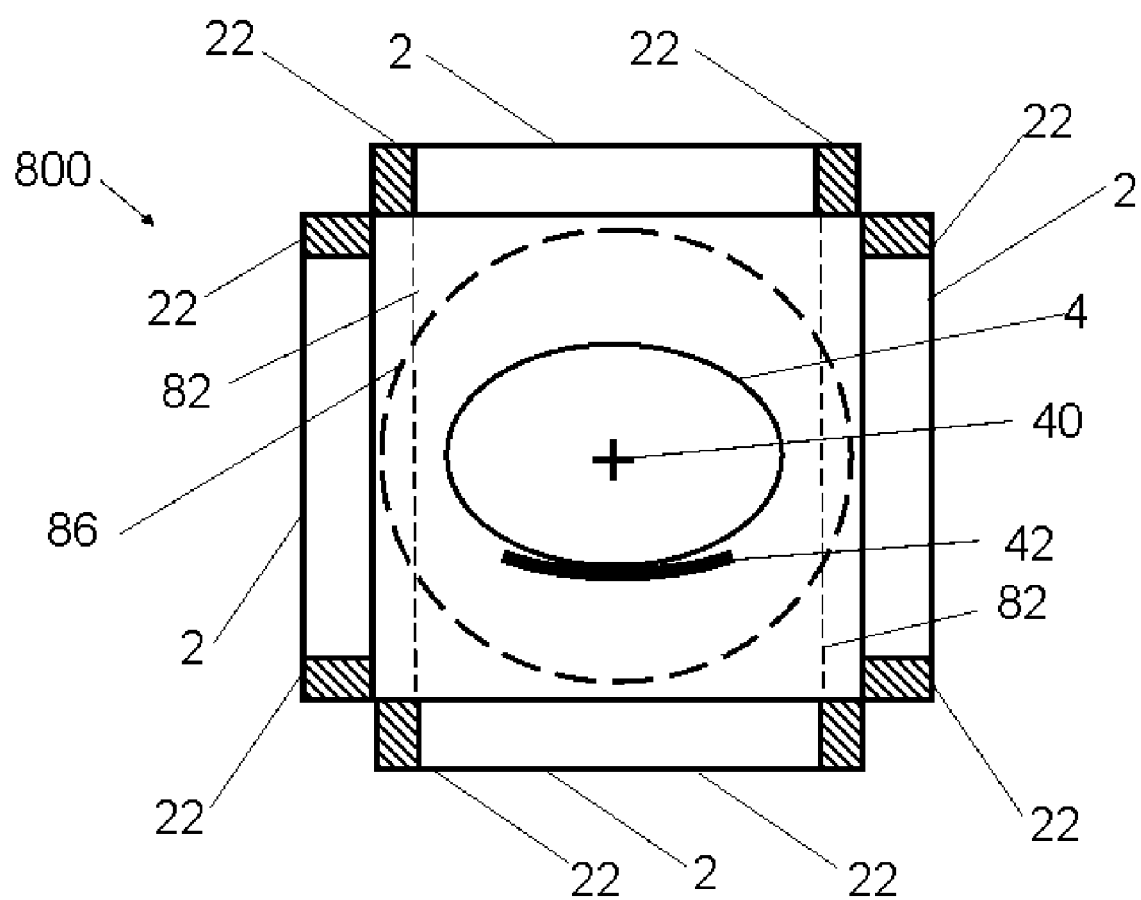
FIG. 8 depicts another embodiment of the current invention showing a nuclear gamma camera equipped with four detectors.

Reference is now made to FIG. 8, depicting an axial view of a simplified schematic diagram of a gamma camera according to an embodiment of the current invention. In this embodiment, system 800 comprises four detectors 2 in a fixed configuration, rotating around inspected portion of a body 4 which is placed on patient table 42. The same configuration is used for inspected portion of a small body or inspected portion of a large body. The geometric center 40 of the camera is marked with a cross. In this embodiment, patient table 42 may be fixed in one position for all sizes of inspected portion of the body; preferably in low position so large objects could be inspected.

Alternatively the patient table may be equipped with an up-down motion system.

Detector 2 is equipped with a collimator (not shown). Detector 2 may have insensitive zone 22 around its perimeter where gamma radiation cannot be recorded.

As can be seen in FIG. 8 the size of the detectors 2 is not limited by the necessity to be close to the inspected body, thus large size detectors, for example 40 to 50 cm or more in the transaxial dimension may be used for imaging small as well as large objects. Additionally, it is apparent from FIG. 8. that the size of the FOV of the detector, demonstrated (for two of the four detectors) by the dashed line 82 prevents missing data as long as the sensitive parts of the detectors are large enough.

Optionally, one, two, three or all the detectors may be fitted with different types of collimator. In this embodiment, the reconstruction algorithm uses the different parameters indicative of the physical properties of each collimator type.

Optionally, at least one of the detectors is fitted with a fan-beam or cone-beam collimator. The usage of these collimators increases the number of photon counts, which improves sensitivity.

Optionally, a cover 86 prevents physical contact between the moving detectors 2 and the patient, eliminating possibility of patient injury and the need for safety measures.

Figure 9:
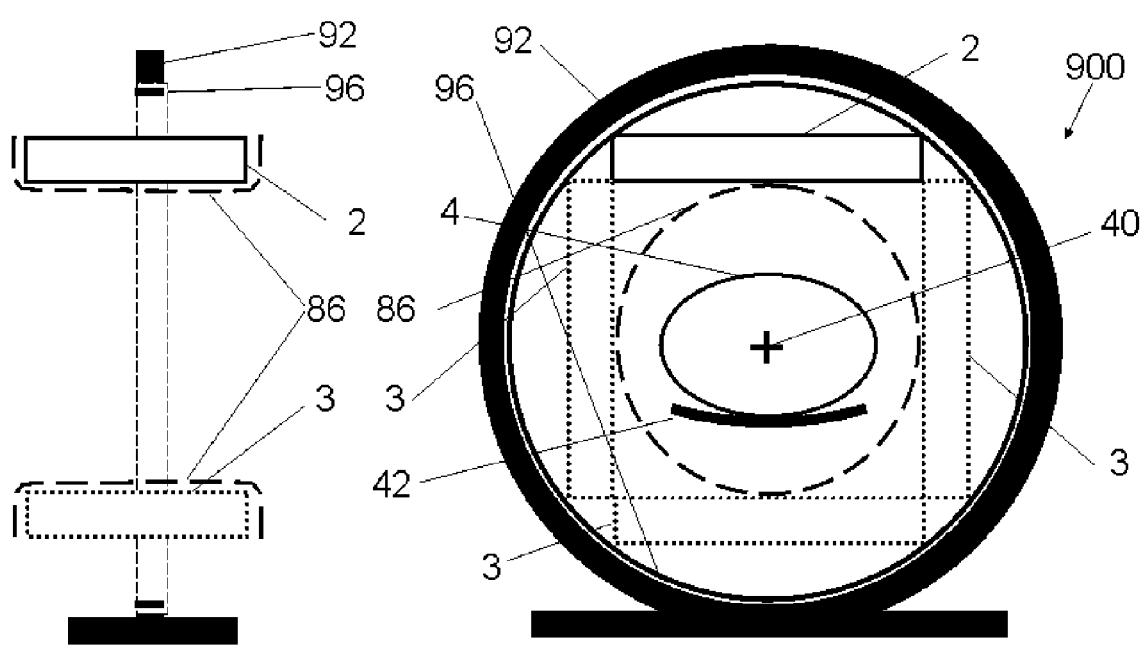
FIGS. 9.*a* and 9.*b* show front and side views respectively of a gantry for a gamma camera according to an embodiment of the current invention.

Reference is now made to FIGS. 9.a and 9.b, showing some details of an axial and side view respectively of a simplified schematic diagram of a gantry for a gamma camera according to an embodiment of the current invention. In this embodiment, system 900 comprises of a rotor 96 rotateable within stator 92. Within rotor 96, at least one detector 2 is attached in a fixed configuration, capable of rotating around inspected portion of a body 4 which is placed on patient table 42. The same configuration is used for inspected portion of a small body or inspected portion of a large body. The geometric center 40 of the camera is marked with a cross. In this embodiment, patient table 42 may be fixed in one position for all sizes of inspected portion of the body; preferably in low position so large objects could be inspected.

Alternatively the patient table may be equipped with an up-down motion system.

Detector 2 is equipped with a collimator (not shown). Detector 2 may have insensitive zone (not shown) around its perimeter where gamma radiation cannot be recorded.

Optionally, the system comprises of one, two or three additional detectors 3. In this drawing, the detectors are at right angle or parallel to each other, but other configurations are possible, for example such as shown in FIG. 6. Alternatively detectors of different sizes may be used.

As can be seen in FIG. 9, the size of the detectors is not limited by the necessity to be close to the inspected body, thus large size detectors may be used for small as well as large objects.

Optionally, several or all the detectors may be fitted with different types of collimator. In this embodiment, the reconstruction algorithm uses the different parameters indicative of the physical properties of each collimator type.

Optionally, at least one of the detectors is fitted with a fan-beam or cone-beam collimator.

Optionally, a cover 86 prevents physical contact between the moving detectors and the patient, eliminating possibility of patient injury and the need for safety measures.

Figure 10:
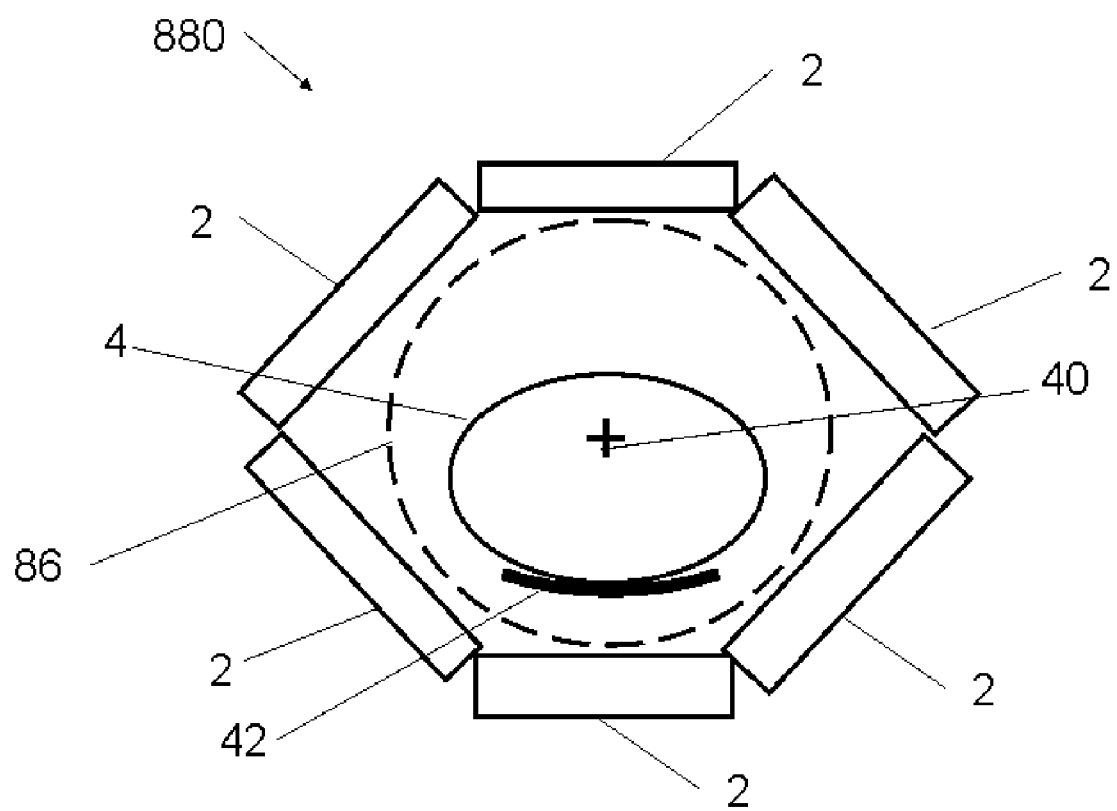
FIG. 10 depicts another embodiment of the current invention showing a nuclear gamma camera equipped with six detectors.

Reference is now made to FIG. 10, depicting an axial view of a simplified schematic diagram of a gamma camera according to an embodiment of the current invention. In this embodiment, system 880 comprises six detectors 2 in a fixed configuration, rotating around inspected portion of a body 4 which is placed on patient table 42. The same configuration is used for inspected portion of a small body or inspected portion of a large body. The geometric center 40 of the camera is marked with a cross. In this embodiment, patient table 42 may be fixed in one position for all sizes of inspected portion of the body; preferably in low position so large objects could be inspected.

Alternatively the patient table may be equipped with an up-down motion system.

Detector 2 is equipped with a collimator (not shown).

As can be seen in FIG. 10, the size of the detectors 2 is not limited by the necessity to be close to the inspected body, thus large size detectors in the transaxial dimension may be used for small as well as large objects.

Optionally, few or all the detectors may be fitted with different types of collimator. In this embodiment, the reconstruction algorithm uses the different parameters indicative of the physical properties of each collimator type.

Optionally, at least one of the detectors is fitted with a fan-beam or cone-beam collimator.

Optionally, a cover 86 prevents physical contact between the moving detectors 2 and the patient, eliminating possibility of patient injury and the need for safety measures.

It is apparent to person skilled in the art that any number of detectors, such as five is also possible. It is also clear that the detectors need not be of same dimensions and may be arranged so that they forms unequal angles with respect to each other.

Figure 11:
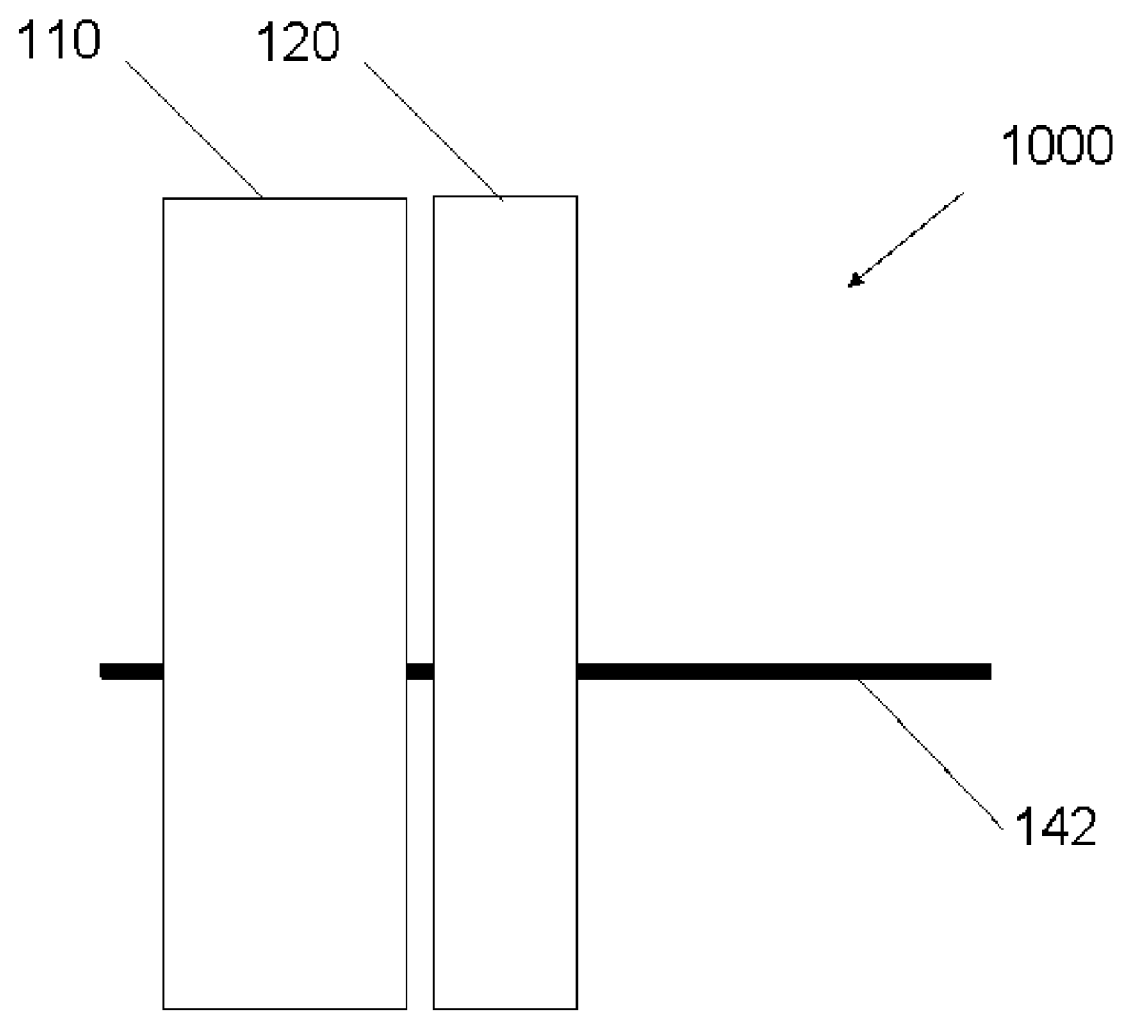
FIG. 11 depicts another embodiment of the current invention showing a system including a nuclear gamma camera and a CT camera.

Reference is now made to FIG. 11, depicting an axial view of a simplified schematic diagram of a system 1000 comprising a gamma camera 110 and a transmission imaging camera 120 according to an embodiment of the current invention. Transmission imaging camera 120 may be a diagnostic quality CT, a low performance CT, or isotope based transmission-imaging camera. The system may be constructed by joining two separate cameras and having one patient table 142 as in FIG. 11. Alternatively, the emission image and transmission image may be taken using two separate cameras and the two images combined by registration of the two images. Alternatively, the transmission image and the emission image may be acquired by the same camera.

In some embodiment of the invention, information related to gamma photon attenuation within the patient body is obtained from the transmission image and used to correct the emission image during WBR or RR iterative reconstruction.

While the invention has been described with reference to certain exemplary embodiments, various modifications will be readily apparent to and may be readily accomplished by persons skilled in the art without departing from the spirit and scope of the above teachings.

It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art.

It is noted that some of the above described embodiments may describe the best mode contemplated by the inventors and therefore include structure, acts or details of structures and acts that may not be essential to the invention and which are described as examples. Structure and acts described herein are replaceable by equivalents which perform the same function, even if the structure or acts are different, as known in the art. Therefore, the scope of the invention is limited only by the elements and limitations as used in the claims. The terms "comprise", "include" and their conjugates as used herein mean "include but are not necessarily limited to".

What is claimed is:

1. A SPECT gamma camera system, comprising:
at least one gamma detector adapted to orbit in a predetermined fixed radius with respect to a patient; analyzer connected to said at least one gamma detector, for analyzing data collected from said at least one gamma detector and reconstructing a SPECT image, using an iterative algorithm belonging to the RR (Resolution Recovery) family of reconstruction algorithms, that reduce line spread function effect.

2. The system of claim 1, wherein a stationary bed is provided for the patient to lie on during data acquisition.

3. The system of claim 1, comprising at least two gamma detectors.

4. The system of claim 1, comprising at least three gamma detectors.

5. The system of claim 1, comprising at least four gamma detectors.

6. The system of claim 1, having at least two gamma detectors, wherein at least two gamma detectors are in fixed position with respect to each other.

7. The system of claim 1, and further comprising means for obtaining a transmission image of the patient.

8. The system of claim 7, wherein the iterative reconstruction algorithm utilizes information obtained from the transmission image in order to correct the emission image.

9. The system of claim 1 wherein said at least one gamma detector is incorporated with a CT scanner and shares the same patient bed to obtain SPECT/CT images in a single bed pass.

10. A SPECT gamma camera system as claimed in claim 1, wherein said detector is larger than 25 cm along the axial dimension.

11. A SPECT gamma camera system as claimed in claim 1, wherein said detector is larger than 40 cm along the axial dimension.

12. A SPECT gamma camera system as claimed in claim 1, wherein said detector is larger than 50 cm along the transaxial dimension.

13. A method for SPECT imaging, the method comprising:
acquiring data related to gamma photons from a patient who received a dose of radiopharmaceutical substance, using at least one gamma detector orbiting in a predetermined fixed radius with respect to the patient;
analyzing the data and reconstructing a SPECT image using an iterative algorithm belonging to the RR (Resolution Recovery) family of reconstruction algorithms; and,
outputting the reconstructed SPECT image or a portion thereof.

14. The method of claim 13, wherein said patient is stationary during data acquisition.

15. The method of claim 13, wherein said reconstructing SPECT image using an iterative algorithm utilizes information regarding attenuation of the gamma photon caused by the patients' body.

16. A method for SPECT imaging as claimed in claim 13, wherein said detector is larger than 25 cm along the axial dimension.

17. A method for SPECT imaging as claimed in claim 13, wherein said detector is larger than 40 cm along the axial dimension.

18. A method for SPECT imaging as claimed in claim 13, wherein said detector is larger than 50 cm along the transaxial dimension.

19. A SPECT gamma camera system, comprising:
at least one gamma detector adapted to orbit in a predetermined fixed radius with respect to a patient; analyzer connected to said at least one gamma detector, for analyzing data collected from said at least one gamma detector and reconstructing a SPECT image, using an iterative algorithm belonging to the WBR (Wide Beam Reconstruction) family of reconstruction algorithms, that reduce line spread function effect.

20. The system of claim 19, wherein a stationary bed is provided for the patient to lie on during data acquisition.

21. The system of claim 19, comprising at least two gamma detectors.

22. The system of claim 19, comprising at least three gamma detectors.

23. The system of claim 19, comprising at least four gamma detectors.

24. The system of claim 19, having at least two gamma detectors, wherein at least two gamma detectors are in fixed position with respect to each other.

25. The system of claim 19, further comprising means for obtaining a transmission image of the patient.

26. The system of claim 25, wherein said iterative reconstruction algorithm utilizes information obtained from the transmission image in order to correct the emission image.

27. The system of claim 19 wherein said at least one gamma detector is incorporated with a CT scanner and shares a same patient bed to obtain SPECT/CT images in a single bed pass.

28. A SPECT gamma camera system as claimed in claim 19, wherein said detector is larger than 25 cm along the axial dimension.

29. A SPECT gamma camera system as claimed in claim 19, wherein said detector is larger than 40 cm along the axial dimension.

30. A SPECT gamma camera system as claimed in claim 19, wherein said detector is larger than 50 cm along the transaxial dimension.

31. A method for SPECT imaging, the method comprising:
acquiring data related to gamma photons from a patient who received a dose of radiopharmaceutical substance, using at least one gamma detector orbiting in a predetermined fixed radius with respect to the patient;
analyzing the data and reconstructing a SPECT image using an iterative algorithm belonging to the WBR (Wide Beam Reconstruction) family of reconstruction algorithms; and,
outputting the reconstructed SPECT image or a portion thereof.

32. The method of claim 31, wherein said patient is stationary during data acquisition.

33. The method of claim 31, wherein said reconstructing SPECT image using an iterative algorithm utilizes information regarding attenuation of the gamma photons by the patients' body.

34. A method for SPECT imaging as claimed in claim 31, wherein said detector is larger than 25 cm along the axial dimension.

35. A method for SPECT imaging as claimed in claim 31, wherein said detector is larger than 40 cm along the axial dimension.

36. A method for SPECT imaging as claimed in claim 31, wherein said detector is larger than 50 cm among the transaxial dimension.

* * * * *